United States Patent [19]
> Houminer et al.

[11] Patent Number: 4,592,373
[45] Date of Patent: Jun. 3, 1986

[54] SMOKING COMPOSITIONS

[75] Inventors: Yoram Houminer, Richmond; Harvey J. Grubbs, Mechanicsville, both of Va.

[73] Assignee: Philip Morris Inc., New York, N.Y.

[21] Appl. No.: 519,785

[22] Filed: Oct. 27, 1983

Related U.S. Application Data

[62] Division of Ser. No. 204,974, Nov. 7, 1980, abandoned.

[51] Int. Cl.[4] .............. A24B 3/12; A24B 15/30; A24B 15/38
[52] U.S. Cl. ................................. 131/276; 131/278
[58] Field of Search ................. 131/276, 278, 277

[56] References Cited

U.S. PATENT DOCUMENTS

| | | | |
|---|---|---|---|
| 4,036,237 | 7/1977 | Teng | 131/276 |
| 4,312,368 | 1/1982 | Houminer | 131/276 |
| 4,318,418 | 3/1982 | Sanders et al. | 131/278 |

FOREIGN PATENT DOCUMENTS 0348471 9/1972 Switzerland ................. 131/278

OTHER PUBLICATIONS

Chem Abst. 1972–1976 Substance Index (33884CS to 33886CS).

*Primary Examiner*—V. Millin

[57] ABSTRACT

This invention provides tobacco and non-tobacco smoking compositions which contain a heterocyclic-hydroxy-substituted carboxylate compound as a flavorant additive.

In one of its embodiments, this invention provides tobacco compositions which contain a heterocyclic-hydroxy-substituted carboxylic acid flavorant additive such as 2-(2-butyl)-3-hydroxy-3-methyl-3-(3-pyridyl)-propionic acid:

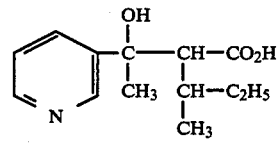

Under smoking conditions the above illustrated heterocyclic-hydroxy-substituted carboxylate additive and its pyrolysis products flavor the mainstream and sidestream smoke. The invention also provides for the method of preparing smoking compositions and the method of comprising the aroma imparted by the burning of a combustible article employing a heterocyclic-hydroxy-substituted carboxylate.

7 Claims, No Drawings

SMOKING COMPOSITIONS

This application is a division of Ser. No. 204,974, filed Nov. 7, 1980 now abandoned.

BACKGROUND OF THE INVENTION

An increasing number of organic materials are being employed as flavoring agents for modifying or improving the flavor and aroma of tobaccos, foodstuffs, beverages and other such consumer products.

The incorporation of flavorants in tobacco products is an important development in the tobacco industry due to the lowered aromaticity of the available tobacco and the increased preference of smokers for filter cigarettes and low delivery cigarettes.

It has been established that alkylpyrazines are natural components of tobacco smoke, and that they most probably are important contributors to tobacco smoke flavor [A. Baggett et al, J. Chromatog, 97, 79 (1974)]. Further, it has been disclosed in the patent literature that addition of alkylpyrazines to tobacco results in an improvement in the flavor of smoking compositions as perceived by a test panel.

British Pat. No. 1,244,068 describes a method for influencing the smoke flavor of tobacco or a tobacco mixture which consists of treating the tobacco with a pyrazine derivative of the following chemical structure:

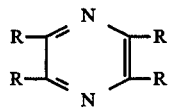

in which each R is independently a hydrogen atom, an aliphatic radical, an alicyclic radical or an aromatic hydrocarbon radical, such radicals having up to 9 carbon atoms, or R is a heterocyclic radical containing 4 to 9 carbon atoms.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyridine and pyrazine compounds to tobacco and foodstuffs as a means of providing flavor or flavor enhancement include U.S. Pat. Nos. 3,684,809; 3,705,158; 3,716,543; 3,754,934; 3,764,349; 3,767,426; and 3,881,025.

U.S. Pat. No. 3,914,227 discloses pyridyl and pyrazyl ketones and their use in altering the organoleptic properties of tobacco and foodstuffs, and U.S. Pat. No. 4,166,869 discloses acylpyrimidines useful as flavorants for the same type of applications.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyridine, pyrazine, pyrimidine, and other heterocyclic derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

In a similar manner, the use of carboxylic acid flavorants for tobacco products has received acceptance because of the desirable aroma and flavor characteristics which they impart to the smoke (J. C. Leffingwell, H. J. Young, and E. Bernasek, "Tobacco Flavoring for Smoking Products," R. J. Reynolds Tobacco Company, Wiston-Salem, 1972). Specifically, acetic acid is commonly used as an ingredient of a Latakia tobacco flavoring formulation (J. Merory, "Food Flavorings," AVI Publishing Company, Incorporated, Westport, Conn. page 420, 1968). Isovaleric acid and 3-methylvaleric acid are major ingredients in a Turkish tobacco flavor formulation (R. H. Stedman and C. D. Stills, U.S. Pat. No. 3,180,340). Desirable flavors have been imparted to cigarette smoke by the addition of 4-ketoacids to tobacco (W. A. Rhode, U.S. Pat. No. 3,313,307).

Numerous methods of adding flavorants to tobacco smoke are known. However, none of the known methods has been found to be completely satisfactory, particularly when the flavorant is a low molecular weight carboxylic acid. Specifically, some of these acids are highly volatile and possess objectionably strong odors that render them difficult to use in bulk amounts required for manufacturing purposes. In addition, some of the volatile acids may impart an undesirable pack aroma.

In an attempt to alleviate some of these problems, carboxylic acids have been incorporated in tobacco as part of a compound (i.e., an organic acid release agent) in such form that upon burning of the tobacco the compound will liberate one or more organic acids imparting a selected and desired flavor and aroma to the smoke. While considerably more satisfactory than earlier attempts, even this technique has evidenced certain drawbacks.

U.S. Pat. Nos. 2,766,145 through 2,766,150 describe a variety of methods for treating tobacco with compounds that release carboxylic acids on pyrolysis. The U.S. Pat. No. 2,766,145 patent describes esters of monohydric and polyhydric compounds. The hydroxy compounds may be aliphatic or aromatic in nature.

The U.S. Pat. No. 2,766,146 describes esters of a sugar acid selected from aldonic acids and uronic acids. U.S. Pat. No. 2,766,150 describes nonvolatile synthetic polymers or condensation products, preferably those related to polyvinyl alcohol and vinyl alcohol-type condensation products. On pyrolysis, the carboxylic acid is liberated to flavor the smoke. These polymers have a distinct disadvantage in that they generally have high molecular weights and are more difficult to solubilize for application on tobacco.

Other references which disclose tobacco flavorant compositions that release carboxylic acids on pyrolysis include U.S. Pat. Nos. 4,036,237 and 4,171,702.

There remains a need for smoking compositions with enhanced flavor and aroma that do not exhibit the various disadvantages of prior art smoking compositions which contain flavorant additives of the types described above.

Accordingly, it is a main object of this invention to provide tobacco and non-tobacco smoking compositions which have incorporated therein a flavorant additive which is characterized by low volatility and low pack aroma.

It is another object of this invention to provide smoking compositions of tobacco and non-tobacco materials, and blends thereof, containing a heterocyclic-hydroxy-substituted carboxylate flavorant additive, which smoking compositions are adapted to impart flavor and aroma to the mainstream and sidestream smoke under smoking conditions.

It is a further object of this invention to provide novel heterocyclic-hydroxy-substituted carboxylate compounds which can be subjected to pyrolysis conditions to release heterocyclic and carboxylic constituents which can enhance the flavor and aroma of smoking compositions and foodstuffs.

Other objects and advantages of the present invention shall become apparent from the accompanying description and examples.

DESCRIPTION OF THE INVENTION

One or more objects of the present invention are accomplished by the provision of a smoking composition which comprises an admixture of (1) combustible filler selected from natural tobacco, reconstituted tobacco, non-tobacco substitutes and mixtures thereof, and (2) between about 0.00001 and 2 weight percent, based on the total weight of filler, of a heterocyclic-hydroxy-substituted carboxylic acid compound corresponding to the formula:

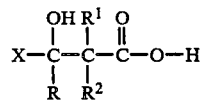

wherein X is a heterocyclic substituent containing between about 2–12 carbon atoms, and any heteroatom in X is selected from oxygen, nitrogen and sulfur; R is a substituent selected from aliphatic, alicyclic and aromatic groups containing between about 1–12 carbon atoms; $R^1$ and $R^2$ are hydrogen or substituents selected from aliphatic, alicyclic and aromatic groups containing between about 1–12 carbon atoms, and $R^1$ and $R^2$ when taken together with connecting elements form an alicyclic structure; or a corresponding salt form of said carboxylic acid compound.

Illustrative of the heterocyclic X substituent in the formula represented above are furyl, tetrahydrofuryl, piperidyl, pyrrolidyl, indyl, pyrazolyl, imidazolyl, pyridyl, pyridazyl, pyrimidyl, pyrazyl, quinolyl, triazolyl, thienyl, tetrahydrothienyl, thiazyl, and the like, and the same type of heterocyclic structures which contain one or more alkyl groups of about 1–4 carbon atom content.

Preferred heterocyclic X substituents in the formula are those selected from pyrazyl and pyridyl radicals corresponding to the chemical structures:

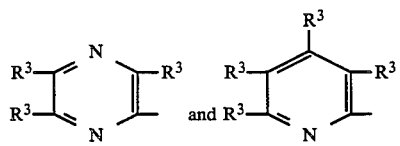

-continued

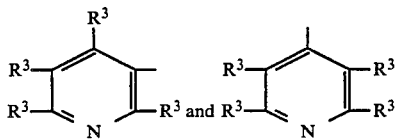

where $R^3$ is a substituent selected from hydrogen and $C_{1-4}$ lower alkyl groups.

Illustrative of the R, $R^1$ and $R^2$ substituents in the formula represented above are groups which include methyl, ethyl, propyl, butyl, pentyl, hexyl, methoxyethyl, ethoxyethyl, cyclopropyl, cyclobutyl, cyclopentyl, cyclohexyl, menthyl, furyl, tetrahydrofuryl, piperidyl, pyrrolidyl, pyrazolyl, phenyl, tolyl, xylyl, benzyl, phenylethyl, methoxyphenyl, naphthyl, pyridyl, pyridazyl, pyrimidyl, pyrazyl, and the like.

As noted previously, $R^1$ and $R^2$ additionally can be hydrogen, and when taken together with the connecting elements form an alicyclic group such as cyclopentyl, cyclohexyl, cycloheptyl, menthyl, and the like.

As noted previously, the heterocyclic-hydroxy-substituted carboxylic acid flavorant additive compound can be employed in the form of a salt. The salt is formed by the interaction of the said carboxylic acid with any compound which is sufficiently basic to form a salt with the carboxylic acid component, and which does not introduce an undesirable off-flavor, and the like.

Illustrative of salt derivatives are those formed by interaction of the carboxylic acid with alkali and alkaline earth basic compounds, e.g., sodium, potassium, lithium and calcium hydroxides and carbonates. Other salt derivatives are those formed by interaction of the carboxylic acid with ammonia and organic amines. Typical organic amines include primary, secondary and tertiary aliphatic and aromatic amines such as amylamine, octylamine, dodecylamine, cyclopentylamine, benzylamine, 2-aminobutanol, monoethanolamine, dipropylamine, dibenzylamine, diethanolamine, pyrrolidine, N-methylpyrrolidine, morpholine, piperidine, piperazine, tripropylamine, tributylamine, tribenzylamine, triethanolamine, and the like.

A heterocyclic-hydroxy-substituted carboxylic acid compound corresponding to the formula represented above is a low volatility flavorant which under normal smoking conditions, or other comparably intensive localized heating conditions, volatilizes and evolves as a gaseous component. Concomitantly, a portion of the heterocyclic-hydroxy-substituted carboxylic acid compound pyrolyzes to yield three separate products which respectively exhibit flavorant properties. These secondary flavorant compounds are released in accordance with the following illustrated reaction mechanism:

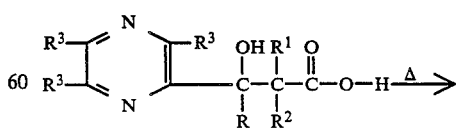

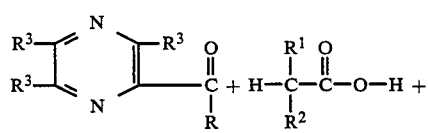

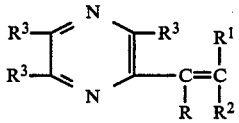

Similar pyrolysis results are obtained when the heterocyclic-hydroxy-substituted carboxylic acid starting material is in the form of a salt, except that less of the ethylene secondary flavorant compound is derived in the pyrolyzate. For example, pyrolysis of a metal carboxylate salt might yield little or no ethylene flavorant in the pyrolyzate.

It is an important aspect of the present invention that the pyrolysis of an amine salt can yield up to four secondary flavorant compounds:

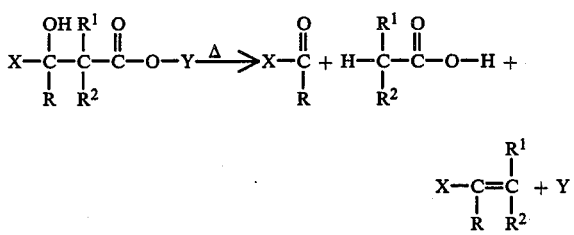

where X, R, $R^1$ and $R^2$ are as previously defined, and Y is a basic organic amine.

Each of the pyrolysis products illustrated above can impart flavor and aroma to tobacco and non-tobacco smoke under smoking conditions.

If it is desirable to produce a large proportion of ethylene compound in the pyrolyzate, then a free acid form of heterocyclic-hydroxy-substituted carboxylic acid is employed as the starting material. As it is apparent, in one of its embodiments this invention provides a convenient pyrolysis method for producing heterocyclic-substituted ethylene derivatives corresponding to the formula:

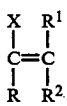

wherein X is a heterocyclic substituent containing between about 2–12 carbon atoms, and any heteroatom in X is selected from oxygen, nitrogen and sulfur; R is a substituent selected from aliphatic, alicyclic and aromatic groups containing between about 1–12 carbon atoms; $R^1$ and $R^2$ are hydrogen or substituents selected from aliphatic, alicyclic and aromatic groups containing between about 1–12 carbon atoms, and $R^1$ and $R^2$ when taken together with connecting elements form an alicyclic structure.

Inclusive of the derivatives which can be prepared by the pyrolysis method is a novel group of heterocyclic-substituted ethylene derivatives corresponding to the formula:

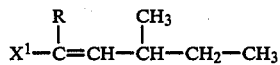

wherein $X^1$ is a heterocyclic substituent selected from pyridyl and pyrazyl radicals containing between about 2–12 carbon atoms, and R is a $C_1$–$C_8$ alkyl substituent.

Preparation of Heterocyclic-hydroxy-substituted Carboxylate Compounds

One method of preparing the heterocyclic-hydroxy-substituted carboxylate compounds of the present invention is by the reaction of a carboxylic acid (or its corresponding salt) with a carbonyl derivative, (e.g., X—CO—R as previously defined), both of which derivatives are appropriately substituted:

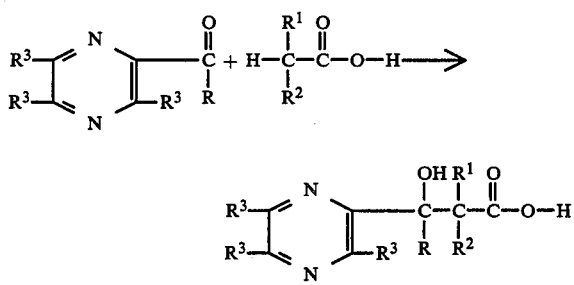

The reaction is conducted in the presence of a strong base such as lithium diisopropylamide, or alkali metal hydride. The strong base initiates the in situ formation of a dianion intermediate:

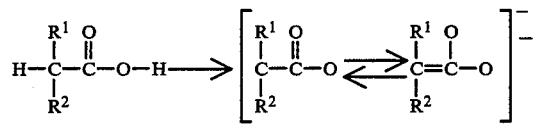

Preferably, the base is added to the carboxylate starting material in an inert solvent medium maintained at a temperature between about −80° and 50° C. and under an inert atmosphere. This procedure is followed by the addition of the heterocyclic-carbonyl compound to the reaction medium at a temperature between about −80° and 25° C.

The resultant heterocyclic-hydroxy-substituted carboxylic acid type of addition products obtained above are odorless, normally liquid compounds of high boiling point. The salt form of the addition products are usually white solids. The salt can be formed by reacting the product with the appropriate base.

Preparation Of Tobacco Compositions

The present invention smoking compositions can be prepared by admixing natural tobacco and/or reconstituted tobacco and/or a non-tobacco substitute with between about 0.00001 and 2 weight percent, and preferably 0.0001–2 weight percent, based on the weight of the smoking composition, of a flavorant additive which corresponds to one of the structural formulae set forth hereinabove in definition of the heterocyclic-hydroxy-substituted carboxylate compounds.

The invention heterocyclic-hydroxy-substituted carboxylate flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5–5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or a clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formations of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

In another embodiment, the present invention also contemplates the incorporation of one of the heterocyclic-hydroxy-substituted carboxylate compounds described above into an article of manufacture which is burned under controlled conditions within the environment of a human habitat. In particular, the combustible articles contemplated are those such as candles, room deodorizers, manufactured fireplace fuel, and the like, the burning of which evolves a gaseous effluent which can be sensed by individuals within olfactory proximity.

As it is apparent, wood logs can also be treated with a solution of a heterocyclic-hydroxy-substituted carboxylate compound prior to ignition in a fireplace.

The incorporation of between about 0.01 and 10 weight percent of a novel heterocyclic-hydroxy-substituted carboxylate compound of the present invention into a candle, for example, can introduce a pleasant aroma or fragrance into a confined living space when the candle is lighted.

In a further embodiment, the present invention provides a method for improving the flavor of a foodstuff (e.g., a meat-containing or meat-simulating product) which comprises contacting the foodstuff with a nontoxic gaseous effluent which is generated by the burning of a combustible material (e.g., a solid fuel) having admixed therewith between about 0.01 and 10 weight percent, based on the weight of combustible content, of a heterocyclic-hydroxy-substituted carboxylate compound of the present invention. Illustrative of one of the applications contemplated is the incorporation of the heterocyclic-hydroxy-substituted carboxylate compound in a smoke-house system for curing meats. Also, an invention substituted carboxylate compound can be incorporated in manufactured carbonaceous fuels (e.g., charcoal briquettes) which are used for broiling raw meat and fish products.

As it is apparent, a present invention heterocyclic-hydroxy-substituted carboxylate compound can be employed with optimal advantage in any application for adding flavor or enhancing the flavor of a foodstuff in which the foodstuff is subjected to a cooking cycle. The substituted carboxylate compound can be admixed with or applied to the surface of foodstuffs prior to or during the cooking phase. The substituted carboxylate compound can be blended with edible solids or liquids to facilitate its application as a flavorant additive. A blend of between about 0.01 and 10 weight percent of substituted carboxylate compound in vegetable oil, for example, is a convenient medium for imparting flavor to foodstuffs in deep-fry operations. The substituted carboxylate compound can also be incorporated as a flavorant additive in prepared sauces, gravies and dressings. Suitable edible vehicles or carriers for a present invention substituted carboxylate compound include fats and oils such as cottonseed oil, soy bean oil, olive oil, and peanut oil; emulsified fats and oils such as butter and margarine; gums such as guar, locust bean, gum arabic, carrageenen; and the like.

The following examples are further illustrative of the present invention. The reactants and other specific ingredients are presented as being typical, and various modifications can be derived in view of the foregoing disclosure within the scope of the invention.

EXAMPLE I

Preparation of 2-(2-Butyl)-3-hydroxy-3-methyl-3-(3-pyridyl)propionic acid

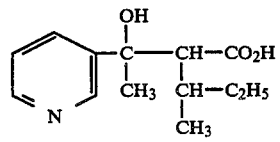

To a solution of diisopropylamine (42.5 grams, 0.42 mole) in 400 milliliters of anhydrous ether at −78° C., is added under nitrogen with stirring a solution of butyllithium in hexane (182.5 milliliters, 0.42 mole). The resulting mixture is stirred at −78° C. for 15 minutes. A solution of 3-methylvaleric acid (23.2 grams, 0.2 mole) in 250 milliliters of ether is added over a period of 20 minutes, keeping the temperature below −45° C. The mixture is allowed to warm up to room temperature and stirred for 3 hours, at which time the formation of the anion is completed.

To the above suspension, cooled to −10° C., is added with stirring a solution of 3-acetylpyridine (24.2 grams, 0.2 mole) in 100 milliliters of ether over a period of 15 minutes. The mixture is allowed to warm up to room temperature and left stirring at room temperature for 16 hours. The mixture is poured with stirring into 500 milliliters of ice-water and an ether layer separates. The pH of the aqueous layer is adjusted to pH 4-5, and then extracted with 5×125 milliliters of methylene chloride. The combined washes are dried over magnesium sulfate and evaporated under reduced pressure to yield 21.6 grams of a brown glossy solid (45.5%). Small amounts of unreacted 3-methylvaleric acid and 3-acetylpyridine present in the product are removed under vacuum (0.1 mm Hg) at 80° C.

Analysis calculated for $C_{13}H_{19}NO_3$: C, 65.80; H, 8.07; N, 5.90 Found: C, 65.81; H, 8.09; N, 5.89

Employing the same procedure as described above, the following heterocyclic-hydroxy-substituted carboxylic acid compounds are prepared by the interaction of the appropriately substituted heterocyclic ketone reactant and acid reactant:

2-Cyclohexyl-3-ethyl-3-hydroxy-3-(2-pyridyl)propionic acid;
2-Methyl-3-hydroxy-3-methyl-3-(2-tetrahydrothienyl)-propionic acid;
2,2-Dimethyl-3-hydroxy-3-phenyl-3-(4-pyridyl)propionic acid; and
2-(2-Butyl)-3-hydroxy-3-methyl-3-(2-pyrrolidyl)propionic acid.

EXAMPLE II

Preparation Of Sodium 2-(2-butyl)-3-hydroxy-3-methyl-3-(3-pyridyl)propionate

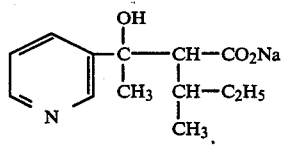

A solution of one gram of hydroxy-acid (Example I) in 25 milliliters of water is treated with one equivalent of sodium carbonate and the solution is stirred for 16 hours. The water is removed under reduced pressure to yield the sodium salt in the form of a white solid.

When the hydroxy-acid starting material is reacted with ammonia or an organic amine, the corresponding ammonium or amine salt form of the carboxylate compound is obtained.

EXAMPLE III

Preparation Of 2-(2-Butyl)-3-hydroxy-3-methyl-3-(2-pyrazyl)propionic acid

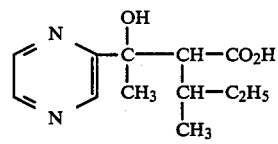

The reaction of 2-acetylpyrazine (21.6 grams, 0.18 mole) with the dianion of 3-methylvaleric acid (from 23.2 grams of acid, 0.2 mole) is conducted in the manner described in Example I, except that tetrahydrofuran is employed as the solvent.

A 31.9 gram quantity of crude product is recovered, and purified as in Example I to yield 14.3 grams of pure product (33.3%).

Analysis calculated for $C_{12}H_{18}N_2O_3$: C, 60.48; H, 7.61; N, 11.76, Found: C, 60.77; H, 7.68; N, 12.00.

Employing the same procedure as described in Example I, the following heterocyclic-hydroxy-substituted carboxylic acid compounds are prepared by the interaction of the appropriately substituted heterocyclic ketone reactant and acid reactant:

2,2-Dimethyl-3-hydroxyl-3-(1-naphthyl)-3-(2,3-diethyl-5-pyrazyl)propionic acid;
3-(2-Butyl-3-pyrazyl)-3-hydroxy-3-phenylpropionic acid;
2-(2-Butyl)-3-hydroxy-3-methyl-3-(2-pyrimidyl)propionic acid; and
2-Methyl-3-hydroxy-3-methyl-3-(2-imidazolyl)propionic acid.

EXAMPLE IV

Preparation Of 2-(2-Butyl)-3-hydroxy-3-methyl-3-(4-pyridyl)propionic acid

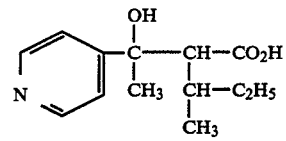

The reaction of 4-acetylpyridine (24.1 grams, 0.2 mole) with the dianion of 3-methylvaleric acid (from 23.2 grams of acid, 0.2 mole) is carried out as described in Example III.

A 23.2 gram quantity of crude material is recovered and purified in the manner described in Example I to yield 6.0 grams of the pure acid (13%).

Analysis calculated for $C_{13}H_{19}NO_3$: C, 65.80; H, 8.07; N, 5.90, Found: C, 65.66; H, 8.30; N, 5.73.

EXAMPLE V

Preparation Of Sodium 2-(2-butyl)-3-hydroxy-3-methyl-3-(4-pyridyl)propionate

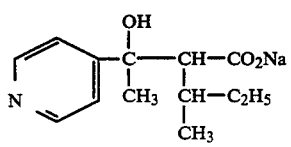

318 milligrams of the hydroxy-acid (Example IV) are converted to the sodium salt by reacting it with sodium bicarbonate as described in Example II. The product is obtained in the form of a white solid in essentially quantitative yield.

EXAMPLE VI

Pyrolysis Of 2-(2-Butyl)-3-hydroxy-3-methyl-3-(3-pyridyl)propionic acid

A 1.5 gram quantity of the hydroxy-acid described in Example I is pyrolyzed at 250° C. for 8 minutes in a flask equipped with a condenser.

Analysis of the pyrolyzate by preparative thin layer chromatography indicates that the product mixture contains 810 milligrams (54%) of a 1:1 mixture of 3-acetylpyridine and 3-methylvaleric acid.

Also separated by preparative thin layer chromatography are 240 milligrams (21.7%) of 1-(3-pyridyl)-1-methyl-2-(2-butyl)-ethylene, the structure of which is confirmed by IR and NMR. The material is distilled at 55°-60° C./0.025 mm Hg. This new compound is characterized by green-floral aroma.

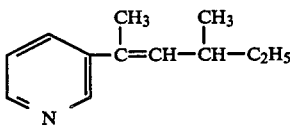

Analysis calculated for $C_{12}H_{17}N$: C, 82.23; H, 9.78; N, 7.99, Found: C, 82.22; H, 9.75; N, 7.92.

EXAMPLE VII

Pyrolysis Of 2-(2-Butyl)-3-hydroxy-3-methyl-3-(4-pyridyl)propionic acid

A 1.35 gram quantity of the hydroxy-acid described in Example IV is pyrolyzed at 250° C. for 15 minutes in an open test tube.

Analysis of the pyrolysis mixture by preparative thin layer chromatography indicates that the product mixture contains 430 milligrams (65%) of 3-methylvaleric acid and 300 milligrams (42.8%) of 4-acetylpyridine.

Also separated by preparative thin layer chromatography are 110 milligrams (11%) of 1-(4-pyridyl)-1-methyl-2-(2-butyl)-ethylene as an oil, the structure of which is confirmed by IR and NMR. This new compound is characterized by green-floral aroma.

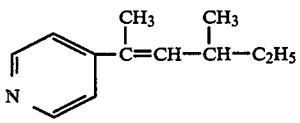

Analysis calculated for $C_{12}H_{17}N$: C, 82.23; H, 9.78; N, 7.99, Found: C, 82.18; H, 9.99; N, 8.05.

EXAMPLE VIII

Pyrolysis Of 2-(2-Butyl)-3-methyl-3-(2-pyrazyl)propionic acid

A 0.82 gram quantity of the hydroxy-acid described in Example III is pyrolyzed at 250° C. for 15 minutes in an open test tube.

Analysis of the pyrolyzate by preparative thin layer chromatography indicates that the product mixture contains 120 milligrams (30%) of 3-methylvaleric acid and 80 milligrams (19%) of 2-acetylpyrazine.

Also separated by preparative thin layer chromatography are 50 milligrams of 1-(2-pyrazyl)-1-methyl-2-(2-butyl)ethylene (8.3%) as an oil, the structure of which is confirmed by IR and NMR. This new compound is characterized by green-floral aroma.

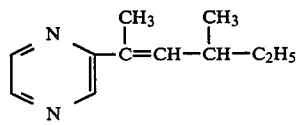

Analysis calculated for $C_{11}H_{16}N_2$: C, 74.95; H, 9.15; N, 15.90, Found: C, 75.02, H, 9.14; N 16.00.

EXAMPLE IX

Pyrolysis Of Sodium 2-(2-butyl)-3-hydroxy-3-methyl-3-(3-pyridyl)propionate

A 1.0 gram quantity of the salt described in Example II is pyrolyzed at 250° C. for 8 minutes in an open test tube. The solid product mixture is extracted with methylene chloride and the solvent removed under reduced pressure to give 210 milligrams of 3-acetylpyridine. The remaining solid is dissolved in water and the pH is adjusted to 1.0 with dilute HCl. The solution is extracted with methylene chloride, and the organic layer is dried over magnesium sulfate and evaporated to give 280 milligrams of 3-methylvaleric acid. No ethylene derivative is detected in the pyrolyzate which differs from the result obtained with the corresponding free acid pyrolyzate (Example VI).

A similar result is obtained when piperidinium 2-(2-butyl)-3-hydroxy-3-methyl-3-(3-pyridyl)propionate is pyrolyzed, except that piperidine is a detected product.

Pyrolysis of calcium 2-(2-butyl)-3-methyl-3-(2-pyrazyl)-propionate and ammonium 2-(2-butyl)-3-methyl-3-(2-pyrazyl)propionate, respectively, yield 3-methylvaleric acid and acetylpyrazine, and no detectable quantity of the ethylene derivative.

EXAMPLE X

Pyrolysis Of Sodium 2-(2-butyl)-3-hydroxy-3-methyl-3-(4-pyridyl)propionate

A 1.0 gram quantity of the salt described in Example V is pyrolyzed and worked up in the manner of Example IX. Analysis of the pyrolyzate indicates that the product mixture contains 160 milligrams of 4-acetylpyridine and 130 milligrams of 3-methylvaleric acid.

None of the ethylene derivative described in Example VII is detected in the pyrolyzate.

A similar result is obtained when dibutylammonium 2-(2-butyl)-3-hydroxy-3-methyl-3-(4-pyridyl)propionate is pyrolyzed, except that dibutylamine is a detected product.

EXAMPLE XI

Pyrolysis Of Sodium 2-(2-butyl-3-hydroxy-3-methyl-3-(3-pyridyl)propionate Impregnated on Cellulose A 73 milligram quantity of the salt is dissolved in 2 milliliters of water and the solution is used to impregnate 1.15 grams of cellulose filter paper. The paper is dried at 110° C. for 30 minutes. The paper is shredded and pyrolyzed at 250° C. for 10 minutes in a flask equipped with a condenser. The residue as well as the distillate obtained are extracted with methylene chloride and the resulting organic solution is dried over magnesium sulfate. Evaporation of the solvent yields 35 milligrams of an oil which is mainly a 1:1 mixture of 3-acetylpyridine and 3-methylvaleric acid.

A small amount of the ethylene derivative described in Example VI is also detected in the product mixture.

EXAMPLE XII

Preparation Of A Smoking Composition Containing A Present Invention Flavorant Cigarettes are fabricated using a typical blend of tobaccos treated with an ethanolic solution of 2-(2-butyl)-3-hydroxy-3-methyl-3-(3-pyridyl)propionic acid, to provide 0.0005 percent of the compound by weight of the tobacco. Untreated control cigarettes are prepared using the identical tobacco blend, and the treated cigarettes are compared to the controls by an experienced smoking panel. The treated cigarettes are found to have more body and more response as compared to the controls.

What is claimed is:

1. A smoking composition comprising an admixture of (1) combustible filler selected from natural tobacco, reconstituted tobacco, non-tobacco substitutes, and mixtures thereof, and (2) between about 0.00001 and 2 weight percent, based on the total weight of filler, of a heterocyclic-hydroxy-substituted carboxylic acid compound corresponding to the formula:

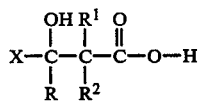

wherein X is a heterocyclic substituent containing between about 2-12 carbon atoms, and any heteroatom in X is selected from oxygen, nitrogen and sulfur; R is a substituent selected from aliphatic, alicyclic and aromatic groups containing between about 1-12 carbon atoms; $R^1$ and $R^2$ are hydrogen or substituents selected from aliphatic, alicyclic and aromatic groups containing between about 1-12 carbon atoms, and $R^1$ and $R^2$ when taken together with connecting elements form an alicyclic structure; or a corresponding salt form of the said carboxylic acid compound.

2. A smoking composition in accordance with claim 1 wherein the non-tobacco substitutes are selected from pectinaceous, cellulosic and carbohydrate materials.

3. A smoking composition in accordance with claim 1 wherein X is a heterocyclic substituent selected from pyrazyl and pyridyl radicals corresponding to the chemical structures:

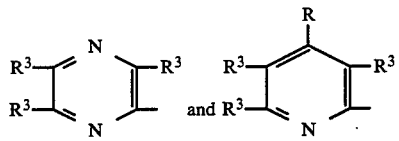

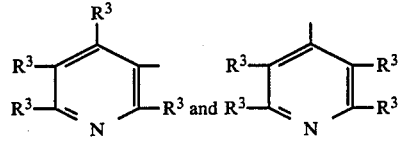

wherein $R^3$ is a group selected from hydrogen and lower alkyl groups.

4. A smoking composition in accordance with claim 1 wherein the carboxylic acid compound is in the form of an alkali metal salt.

5. A smoking composition in accordance with claim 1 wherein the carboxylic acid compound is in the form of an ammonium or organic amine salt.

6. A method of preparing a smoking composition which is adapted to impart flavoring to the mainstream and sidestream smoke under smoking conditions, which method comprises incorporating into natural tobacco, reconstituted tobacco or non-tobacco substitute between about 0.00001 and 2 weight percent, based on composition weight, of a flavorant additive corresponding to the formula:

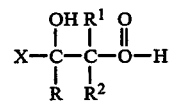

wherein X is a heterocyclic substituent containing between about 2-12 carbon atoms, and any heteroatom in X is selected from oxygen, nitrogen and sulfur; R is a substituent selected from aliphatic, alicyclic and aromatic groups containing between about 1-12 carbon atoms; $R^1$ and $R^2$ are hydrogen or substituents selected from aliphatic, alicyclic and aromatic groups containing between about 1-12 carbon atoms, and $R^1$ and $R^2$ when taken together with connecting elements form an alicyclic structure; or a corresponding salt form of the said flavorant additive.

7. A method of improving the aroma imparted by the burning of a combustible article of manufacture within the environment of a human habitat, which method comprises incorporating into said article of manufacture prior to its combustion between about 0.01 and 10 weight percent, based on the weight of combustible content, of a heterocyclic-hydroxy-substituted carboxylic acid compound corresponding to the formula:

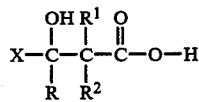

wherein X is a heterocyclic substituent containing between about 2-12 carbon atoms, and any heteroatom in X is selected from oxygen, nitrogen and sulfur; R is a substituent selected from aliphatic, alicyclic and aromatic groups containing between about 1-12 carbon atoms; $R^1$ and $R^2$ are hydrogen or substituents selected from aliphatic, alicyclic and aromatic groups containing between about 1-12 carbon atoms, and $R^1$ and $R^2$ when taken together with connecting elements form an alicyclic structure; or a corresponding salt form of the said carboxylic acid compound.

* * * * *

UNITED STATES PATENT AND TRADEMARK OFFICE
CERTIFICATE OF CORRECTION

PATENT NO. : 4,592,373
DATED : June 3, 1986
INVENTOR(S) : Yoram Houminer and Harvey J. Grubbs It is certified that error appears in the above-identified patent and that said Letters Patent is hereby corrected as shown below:

TITLE PAGE

[62] After November 7, 1980 delete ", abandoned".

ABSTRACT

Line 6 after the formula delete "comprising" and insert --improving--.

Col. 1, line 5, after 1980 delete "now abandoned".

Signed and Sealed this

Seventh Day of April, 1987

Attest:

DONALD J. QUIGG

Attesting Officer

Commissioner of Patents and Trademarks